United States Patent [19]
Alexay

[11] Patent Number: 5,584,557
[45] Date of Patent: Dec. 17, 1996

[54] HIGH EFFICIENCY COMPACT ILLUMINATION SYSTEM

[75] Inventor: Christopher C. Alexay, Walpole, N.H.

[73] Assignee: Janos Technology Inc., Townshend, Vt.

[21] Appl. No.: 424,042

[22] Filed: Apr. 19, 1995

Related U.S. Application Data

[63] Continuation-in-part of Ser. No. 224,655, Apr. 6, 1994, Pat. No. 5,428,222.

[51] Int. Cl.⁶ ..................................................... F21V 7/09
[52] U.S. Cl. ............................ 362/32; 362/302; 362/346
[58] Field of Search .............................. 362/32, 297, 298, 362/302, 346, 347; 250/339.07, 339.12, 339.13, 343, 353; 356/436, 437

[56] References Cited

U.S. PATENT DOCUMENTS

| | | | |
|---|---|---|---|
| 2,064,880 | 12/1936 | Bostic | 362/298 |
| 3,959,660 | 5/1976 | Tolliver | 250/343 |
| 4,241,382 | 12/1980 | Daniel | 362/255 |
| 4,735,495 | 4/1988 | Henkes | 362/347 |
| 4,808,825 | 2/1989 | Miyatake et al. | 250/343 |
| 4,956,759 | 9/1990 | Goldenberg et al. | 362/297 |
| 4,958,076 | 9/1990 | Bonne et al. | 250/343 |
| 5,254,858 | 10/1993 | Wolfman et al. | 250/353 |

*Primary Examiner*—Ira S. Lazarus
*Assistant Examiner*—Alan B. Cariaso
*Attorney, Agent, or Firm*—Herbert M. Wolfson

[57] ABSTRACT

An improved illumination system employing two concave reflecting mirrors and a non-imaging reflector to concentrate energy (light) more efficiently is disclosed.

6 Claims, 10 Drawing Sheets

HIGH EFFICIENCY COMPACT ILLUMINATION SYSTEM

CROSS REFERENCE TO RELATED APPLICATION

This application is a continuation-in-part of U.S. application Ser. No. 08/224,655 filed Apr. 6, 1994 and allowed Dec. 2, 1994 for "A Spectral Analyzer and Method of Using Same" now U.S. Pat. No. 5,428,222.

FIELD OF THE INVENTION

The present invention relates to an illumination system disclosed in the prior. application for use in the spectral analyzer that is also disclosed and claimed therein. Specifically, the present invention relates to an illumination system which images the energy from a light source into the input aperture of a non-imaging reflector in a very efficient manner.

BACKGROUND OF THE INVENTION

U.S. Pat. No. 4,956,759; hereinafter referred to as "Philips" patent, discloses an illumination system which includes a light source, a pair of concave mirrors positioned to collect substantially all of the light from the source, and a non-imaging optic having an input aperture positioned to collect substantially all the light and re-direct it in a somewhat controlled manner.

The second concave mirror, as disclosed in the Philips patent, is of a geometry such that a linear geometry is prohibited. Since the second concave reflector is forming an image of the source at a point remote rather than proximate to the source, the centers of curvature of the concave mirrors and the source can at best exist in a co-planar format. Such a geometry is disadvantageous for several reasons: (1) This geometry requires the incorporation of larger packaging (envelope); (2) This geometry requires greater complexity of mechanics with corresponding greater costs; and, (3) as a result of its departure from a common centerline, this geometry exhibits greater sensitivity to alignment errors. The ability to produce illumination beams of low angular divergence, a direct function of the non-imaging optic, is to transform, by some factor, the angle at which light enters the input aperture to some lesser angle upon departure through the exit aperture. Generally, the greater the angle of divergence entering a non-imaging optic, the greater the angle exiting the non-imaging optic. The illuminating systems of the prior art produce angles as great as 90 degrees to the non-imaging optics centerline, entering the aperture. In contrast, the object of the geometry of the present invention is to allow for the rays of greatest divergence to enter the non-imaging optic at approximately 65 degrees; and, thus, to be much more efficient in the concentration of energy than the designs of the prior art.

Furthermore, an all spherical version of the design disclosed in the Philips patent, would result in the formation of an asymmetrical energy distribution at the entrance aperture of the non imaging optic. Additionally, fabrication of an all spherical version of the design disclosed in the Philips patent (with the second concave reflectors source and image positioned with minimal displacement and, correspondingly, minimal aberration) would be extremely difficult.

It is an object of this invention to provide an illumination system that is more efficient in concentrating energy than prior art systems.

Another object is to produce illumination beams of lower angular divergence than the prior art.

It is also an object of the present invention to provide a system that displays a relatively low sensitivity to alignment errors.

A further object of the invention is to provide a system wherein the envelope size is minimal compared to prior designs, and wherein the complexity of the mechanics is reduced with corresponding reduction in fabrication costs.

A still further object is to provide an illumination system which is adaptable to a wide variety of instruments which use a light source, including but not limited to microscopes, slide projectors, surgical instruments, spectrometers, ophthalmoscopes, and endoscopes.

SUMMARY OF THE INVENTION

The objects are accomplished by an illumination system, comprising a light source; a first concave reflective surface or mirror positioned to collect light from the light source within a first half sphere space and reflect or image the collected light to produce a first image of the light source at a point remote from the source; a second concave reflective surface or mirror which collects light from the source which exceeds the boundary of the first concave mirror to collect a second half sphere space of light, the second mirror reflects or images the second half space of light to produce a second image of the light source at a point proximate to the light source where the first concave mirror reflects or re-images the light collected from the second concave mirror to provide a third image of the light source at the remote point where the first image is produced; and a non-imaging reflector having an input aperture positioned to receive substantially all of the light from the first and third images of the light source.

Thus the objects are achieved with a high efficiency compact illumination system. The first concave mirror is of a form which produces a first image of the light source at a point remote therefrom. A second concave reflective surface is included to collect light that exceeds the boundaries of the first concave mirror, and images the source at a point proximate thereto. It is also the function of the first concave reflective surface to collect this light reimaged by means of the second concave mirror, and produce a third image of the light source at a point remote therfrom. The input aperture of the non-imaging optical member is positioned to collect substantially all of the light, in the form of the first and third images produced by the two concave reflecting mirrors, and is manipulated in a manner to reduce and confine the angle of divergence of light which issues from its exit aperture.

According to a preferred embodiment, the first and second mirrors are profiles so that the first and third images are accomodated by the input aperture of the non-imaging optic. This embodiment has the first mirror as an elliptical concave reflector with its first focus at the source location and its second focus located some distance from the source, corresponding with the entrance aperture of either the homogenizing element or the non-imaging optic. The second concave mirror has the preferred spherical form with its center of curvature located proximate to the source position. In the most preferred system, the light source, the centers of curvature of the mirrors, the non-imaging optic, and all of the images lie in a common line.

An important use for this illumination system is as a high efficiency optical collector in a spectral analyzer. The spectral analyzer, therefore, includes a high efficiency optical collector having a first concave reflector portion and an opposed second concave reflector portion with an exit passage therethrough. A source for light emitting of a predetermined wavelength range is positioned in the collector so that the emitted light is collected and directed by the reflector portions to the exit passage. A specimen holder is positioned adjacent the exit passage of the collector, and it has entrance and exit ends with windows therein.

At the exit end of the specimen holder is the entrance end of an elongated reverse non-imaging optical member. This optical member has a peripheral wall reflecting light rays entering it through the exit window of the holder to reduce the angle of the rays relative to the optical axis of the optical member as they pass therethrough. At the exit end of the optical member is a detector assembly including at least one photodetector sensitive to a predetermined wavelength of light and at least one optical filter disposed between the optical member and the photodetector to pass light of the predetermined wavelength.

The first portion of the collector may conveniently be a concave spherical surface or an ellipsoidal surface.

The non-imaging optical member may have a compound parabolic configuration, although it may also have a configuration selected from the group of general conics, aspheres and splines.

The windows of the specimen holder filter a frequency or pass a frequency of a predetermined wavelength range. The detector assembly includes an optical concentrator between the filter and the photodetector. A multiplicity of cooperating photodetectors and cooperating filters sensitive to light rays of different wavelength ranges may be provided in the detector assembly.

The specimen holder may be a tubular element for containing a gas or include means for supporting a translucent solid specimen, or include means for locating the surface of a specimen at an angle to the longitudinal axis of the holder. The specimen holder may also be a solid translucent light guide which permits evanescent spectral energy absorption at the interface with a specimen disposed on its periphery.

If desired, a chopper may be provided to pulse the light rays passing into the specimen holder. Although light rays in the infrared wavelength are generally preferred, ultraviolet and visible light may also be employed.

In use, power is provided to the light source to effect emission of light rays which are collected and reflected to the exit aperture from the collector and into the specimen holder containing a specimen to be analyzed. The specimen interacts with the light rays to provide spectral indicia of the components thereof.

The light rays are then passed through the elongated non-imaging optical member to reduce the angle of the light rays entering thereinto relative to the optical axis of the optical member. The light rays exiting the optical member then impinge upon a photodetector to generate signals indicative of a component of the specimen, and these signals from the photodetector are analyzed.

Preferably, the light rays exiting the optical member are directed through a filter prior to impinging upon the photodetector, and the light rays exiting the optical member are directed through an optical concentrator prior to the photodetector.

DETAILED DESCRIPTION OF THE PREFERRED EMBODIMENT

Figure 1:
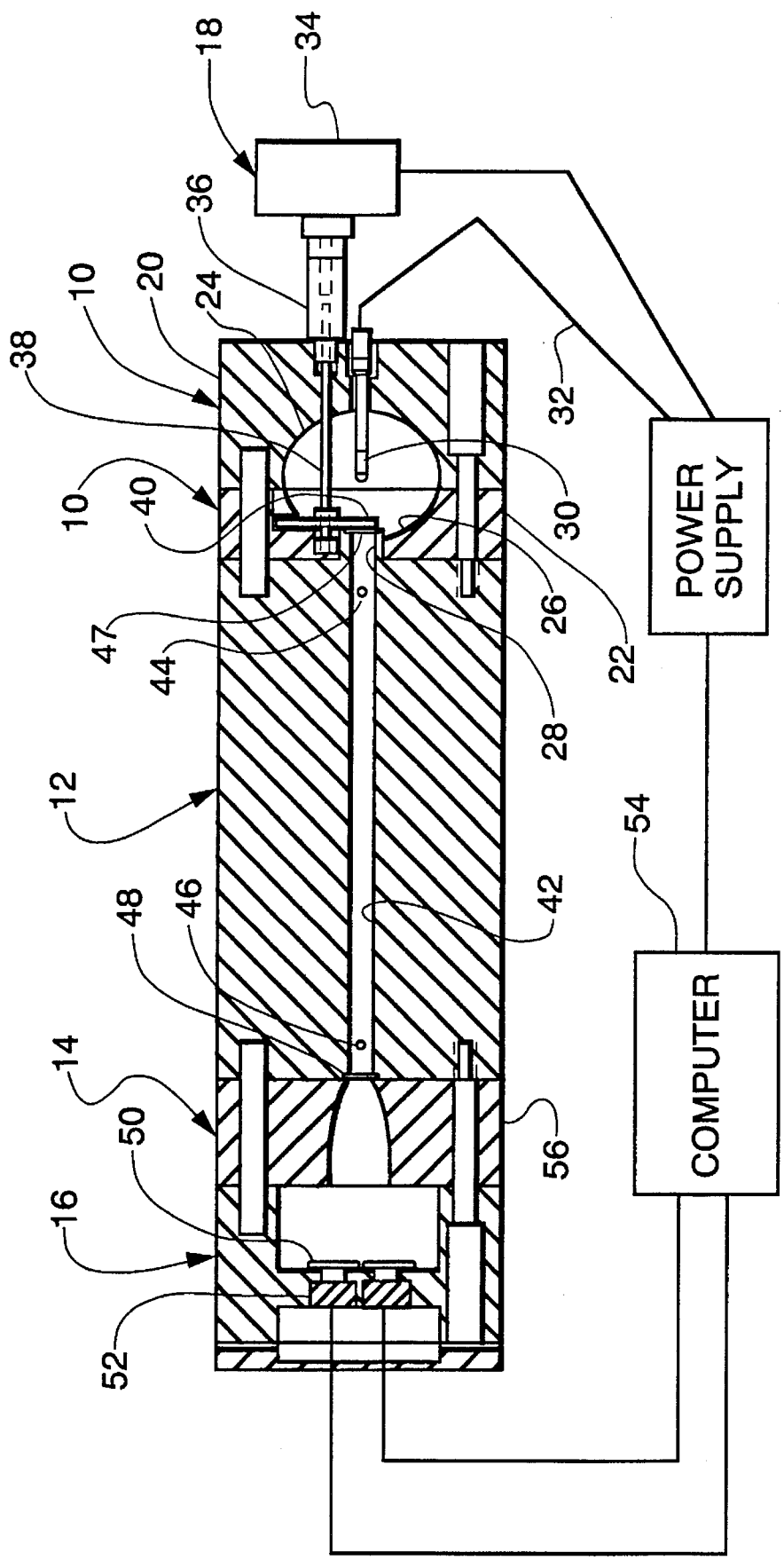
FIG. 1 is a partially diagrammatic view of a spectral analyzer for gases and liquids embodying the present invention.
Figure 2:
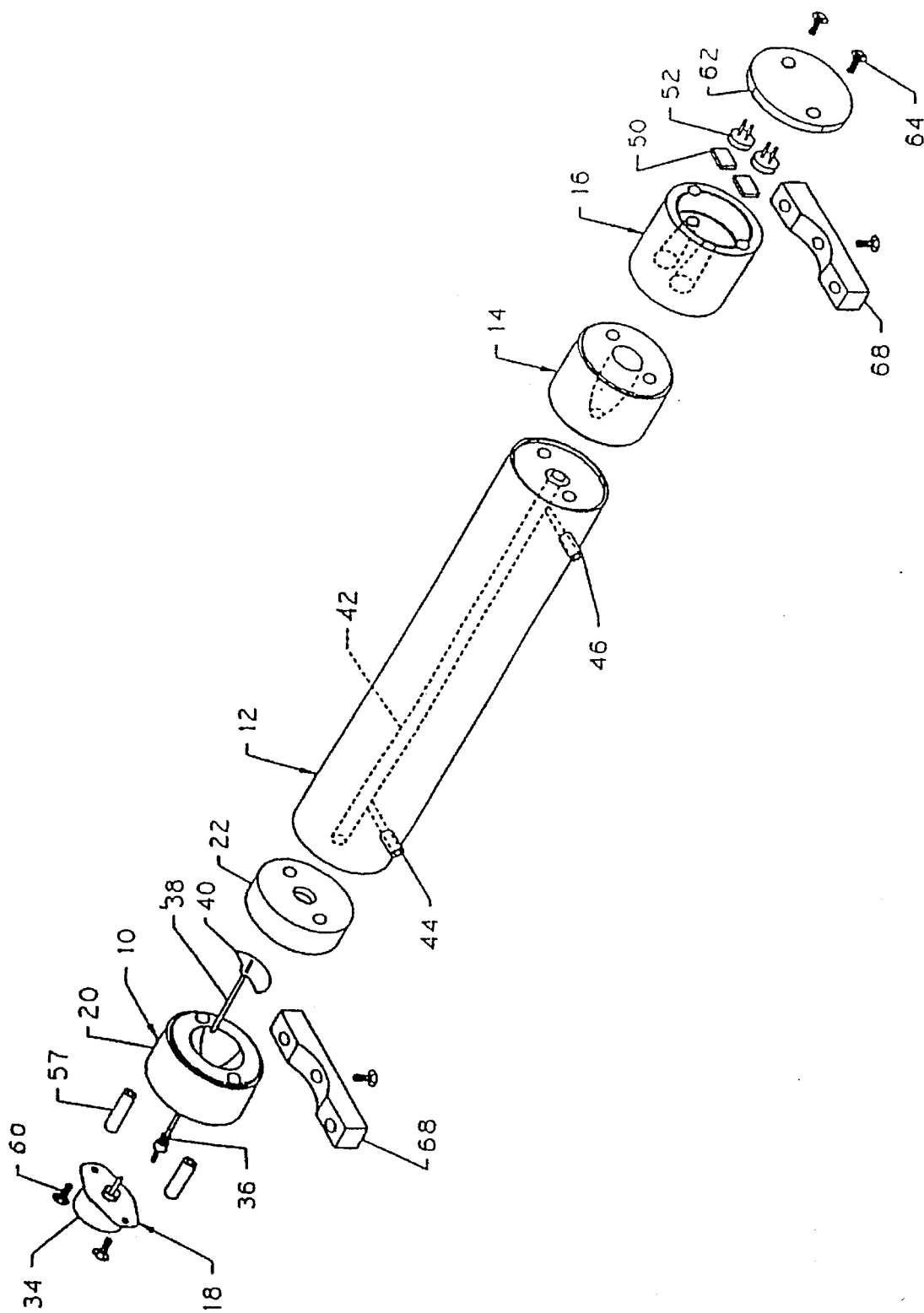
FIG. 2 is an exploded view of the analyzer of FIG. 1.

Turning first to FIGS. 1 and 2, therein diagrammatically illustrated in the analyzer embodying the illuminating system of the present invention. It is generally comprised of a light source and collector generally designated by the numeral 10, a specimen holder generally designated by the numeral 12, a non-imaging optical member generally designated by the numeral 14, and a detector assembly generally designated by the numeral 16. Also shown is a chopper assembly generally designated by the numeral 18.

The collector 10 is conveniently comprised of a pair of blocks 20 and 22 providing a concave spherical surface 24 and an opposing spherical surface 26, respectively. A coaxially disposed aperture 28 is provided in block 22. A light source 30 is coaxially disposed in the block 20 so that the light rays generated by it will be reflected from the surfaces 24, 26 and directed to the aperture 28. The light source or emitter 30 is connected to a power source (not shown) by the cable 32.

The chopper assembly 18 includes a drive motor 34 with a coupling 36 which transmits rotary motion to the drive shaft 38 upon which is mounted the chopper blade 40 which extends across the aperture 28. Power is supplied to the motor 34 through the cable 35.

The specimen holder 12 in this embodiment is adapted for passage of a gas or liquid therethrough and comprises a block having a coaxial cavity 42 therein. Inlet and outlet ports 44 and 46 allow flow therethrough of the gas or liquid to be analyzed, and the windows 47, 48 at each end thereof retain the gas or liquid therein.

After passage through the specimen in the holder 12, the light rays exit through the window 48 into the non-imaging optical member 14. As the light rays pass therethrough, they are reflected from the wall surface defining the passage 50 so that they exit at angles which are smaller relative to the optical axis of the passage 50, i.e., they are travelling more closely to the optical axis.

Upon exiting the optical member 14, the light rays pass into detector assembly 16 where they pass through filters 50 and are incident upon the photodetectors 52 which measure the intensity of the filtered light rays. Signals are outputted through the leads 55 to a computer 54 which interprets the intensity to determine concentration of the components being analyzed.

As more specifically illustrated in FIG. 2, a convenient assembly is provided by the several blocks and tubes which are joined by pins or dowels 57 seated in aligned recesses 58 and secured therein by adhesive, friction or set screws. A flange on the chopper motor 34 is secured to the block 20 by threaded fasteners 60. A removable end cap 62 is secured by fasteners 64 to the block 66 which provides the housing of the detector assembly 16. This entire assembly is supported on mounts 68 which may be secured to any suitable support (not shown).

Figure 3:
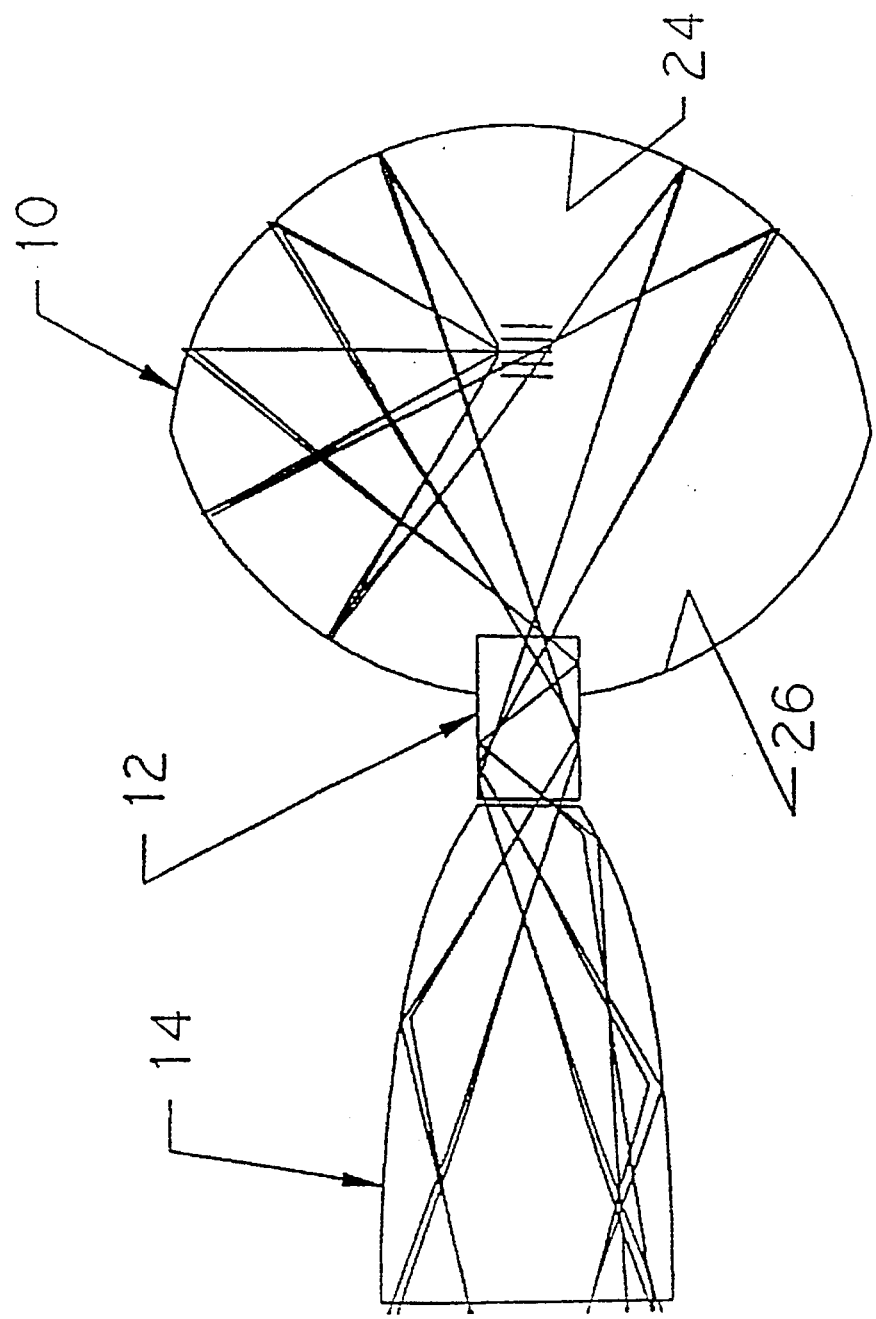
FIG. 3 is a diagrammatic view of the collector, gas cell and parabolic concentrator showing traces of the light rays passing therethrough.

Turning next to FIG. 3, therein schematically illustrated are ray traces showing light rays emitted by the source 30 being reflected by the surfaces 24, 26 to the exit aperture 28 which extends to the window 28 (seen in FIG. 1) and thence into the specimen holder 12. The light rays are reflected from its surfaces and pass therethrough and through the specimen contained therein until they exit the holder 12 and pass into the non-imaging optical member 14. The light rays are reflected from the surface defining the passage through the member 14 so that they exit at a relatively shallow angle relative to the optical axis 72 of the assembly.

Figure 4A:
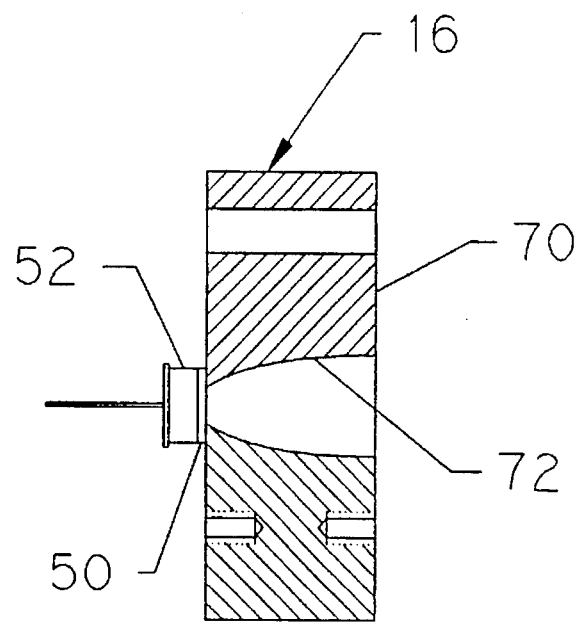
FIGS. 4a and 4b are partially diagrammatic views of a ray concentrator for the detector assembly to concentrate rays impinging upon the photodetectors.
Figure 4B:
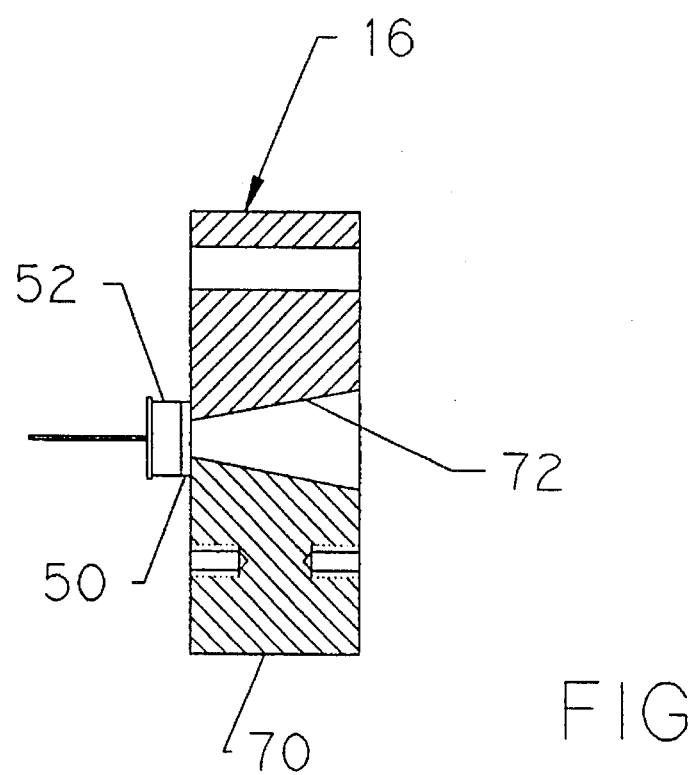

Although not essential, the effectiveness of the apparatus may be increased by including within the detector assembly 16 light guides or concentrators to direct light rays onto the photodetectors 52. As seen in FIGS. 4a and 4b, the detector housing 70 may incorporate a plurality of converging passages 72 (only one is shown) which have exit ends aligned with the photodetectors 52.

Figure 5A:
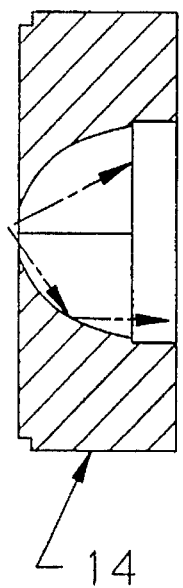
FIGS. 5a–5d are diagrammatic views of different configurations of nonimaging optical members which may be utilized in the present invention.
Figure 5B:
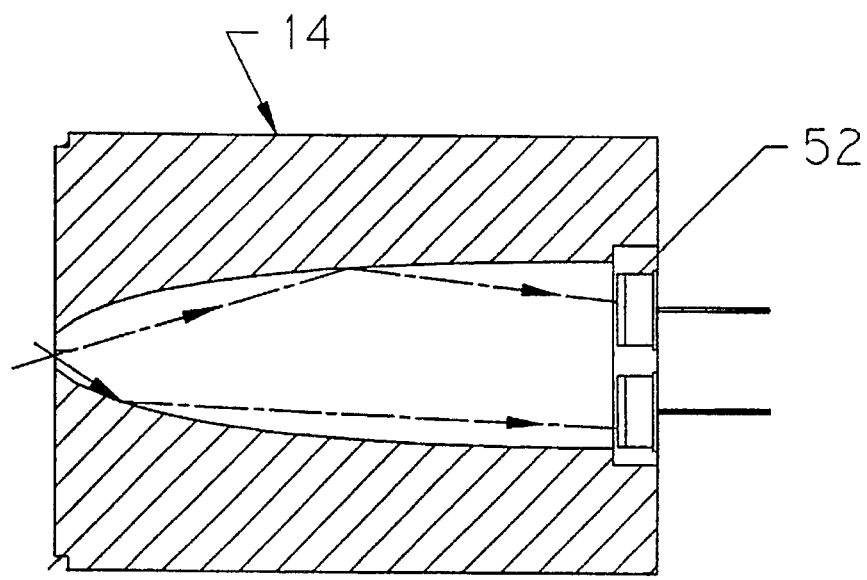
Figure 5C:
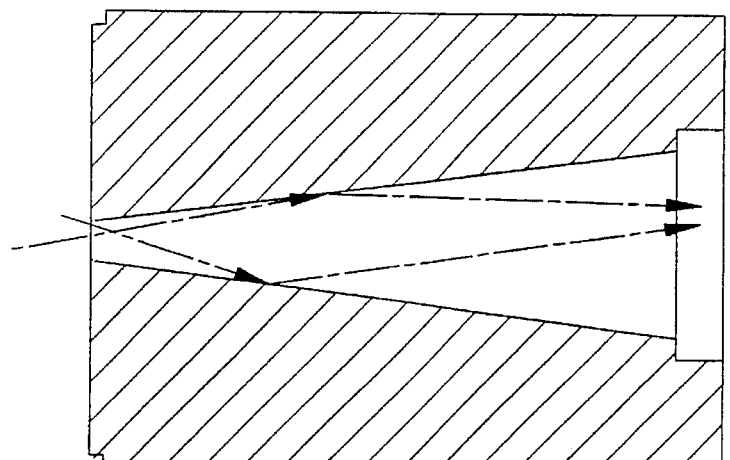
Figure 5D:
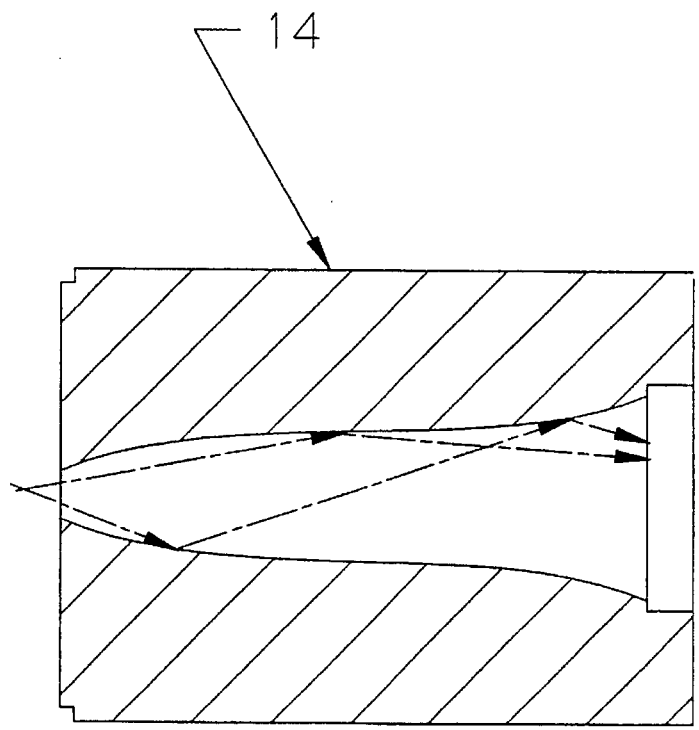

Illustrated diagrammatically is FIGS. 5a–5d are several configurations of nonimaging optical members to reduce the angle of light rays passing therethrough as indicated by the ray traces. FIGS. 5a and 5b are other types of aspheric surfaces; FIG. 5c shows a conic surface; and FIG. 5d shows use of the surface of a spline.

Figure 6A:
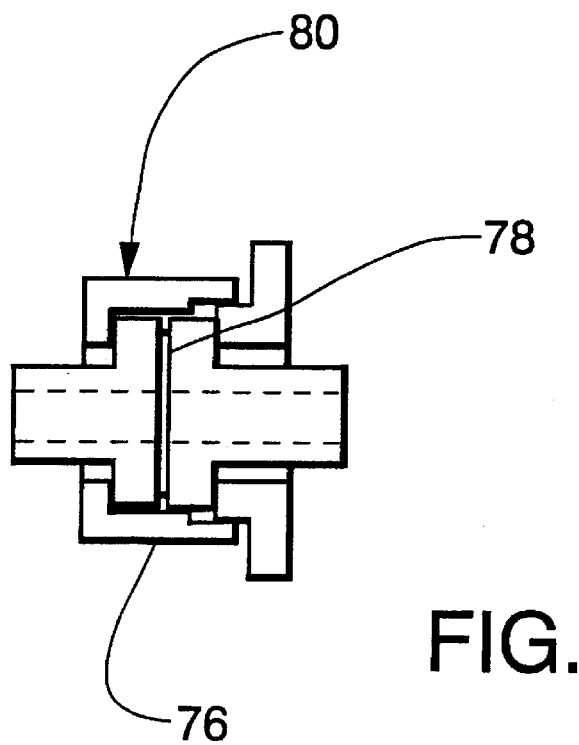
FIGS. 6a–6c are diagrammatic views of other types of specimen holders which may be used.
Figure 6C:
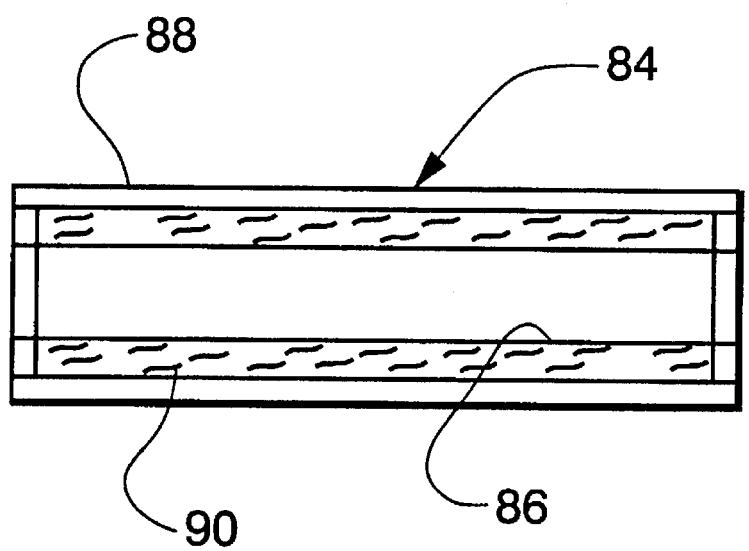
Figure 6B:
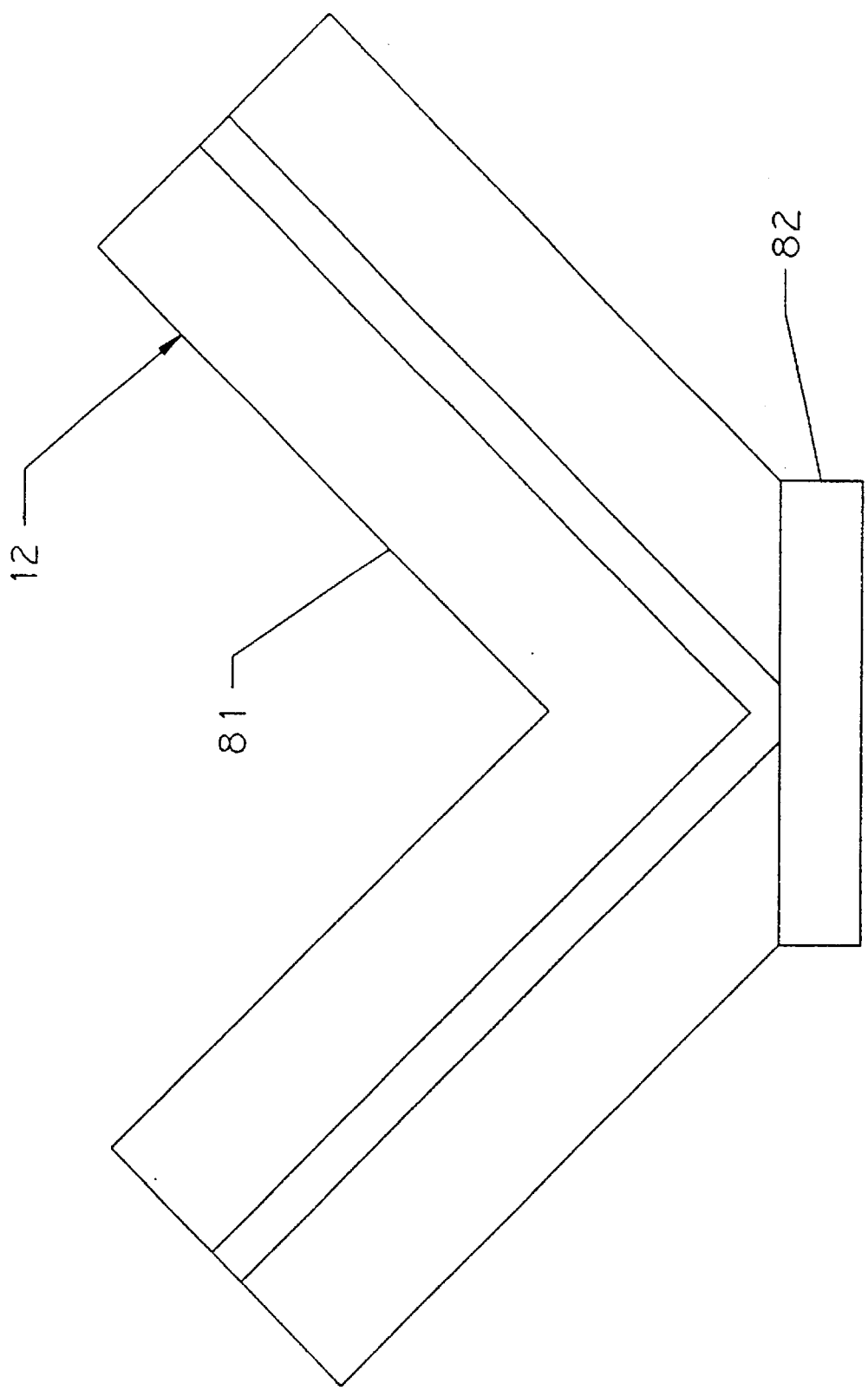

As seen in FIGS. 6a–6c, the specimen holder may have a number of constructions depending upon the type of material being analyzed, and the nature of the action of the specimen on the light rays, e.g, absorption, reflection and evanescence.

The embodiment illustrated in FIGS. 1 and 2 uses a specimen holder in which the light rays are transmitted through the specimen and is generally adapted for use with liquids and gases. FIG. 66 illustrates a specimen holder 80 for an opaque solid providing a V-shaped light guide 81 which has the specimen 82 supporting at its apex so that the light rays are reflected from its surface. FIG. 6c illustrates a specimen holder 84 in which the light guide 86 extends through a tube 88 containing a liquid specimen 90 and attenuation at the surface of the light guide 86 is effected.

As previously described, the light rays exiting the non-imaging optical member desirably pass through filters which cooperate with an associated photodetector. These filters may allow only a light of narrow wavelength range to pass therethrough or may selectively remove light of a narrow range depending upon the band wavelength(s) being measured by the detector.

As a direct result of the optics the light rays are directed at angles approaching normal to the filter and the spectral filters are able to function more efficiently in the effort to analyze the optical energy after its interaction with the sample. The filters are typically designed to allow for a specific wavelength band width to pass through the filter while rejecting all other energy. Therefore, if the filters are selected to have a bandwidth which closely matches the absorption band of the sample in the compartment, they will be able to alert the system to the absence of optical energy which is of a wavelength synonymous with a particular material. This allows one to identify the presence of some known material in the sample compartment due to its absorption.

Because of its efficiency and compact size, the spectral analyzer may be fabricated as a small battery operated gas detection instrument to make possible easy and economical atmospheric monitoring for a wide variety of gases. The components may be fabricated readily and relatively economically so that the cost to the user is relatively small by comparison to existing units which are much larger, heavier and not truly portable. Two components may be combined such as the non-imaging optical member and detector assembly as seen in FIG. 5d.

The light collection and channeling properties of the system are highly efficient, and the components may be designed so as to permit modular manufacturing and assembly of the three major components (source/collector, specimen holder, energy collector/re-director) into a multitude of geometries. The light collecting and channeling efficiency of the system has industrial applicability in gas analysis, fluid analysis, fluorescence analysis and generally any application where spectral information can be obtained by means of sample/optical energy interaction.

Moreover, as a result of this highly efficient assembly, four or more different components in a specimen may be monitored by providing a series of different photodetectors and cooperating filters, each monitoring light of a different wavelength indicative of the different components.

In the optical collector, the two reflective surfaces cooperate with the light emitter placed therebetween. In the optical system described above, the components are arranged so as to allow for maximum solid angle radiometric efficiency.

The relationship of focal points and overall geometry of the collecting optic shells defines their collection efficiency. The first half of the optical shell has its vertex located behind the centerpoint of the optical source. This particular section may have one of two general geometries. The first is the simple sphere. The radius of the sphere is selected so as to produce an image of the source at the window to the specimen holder.

Figure 7:
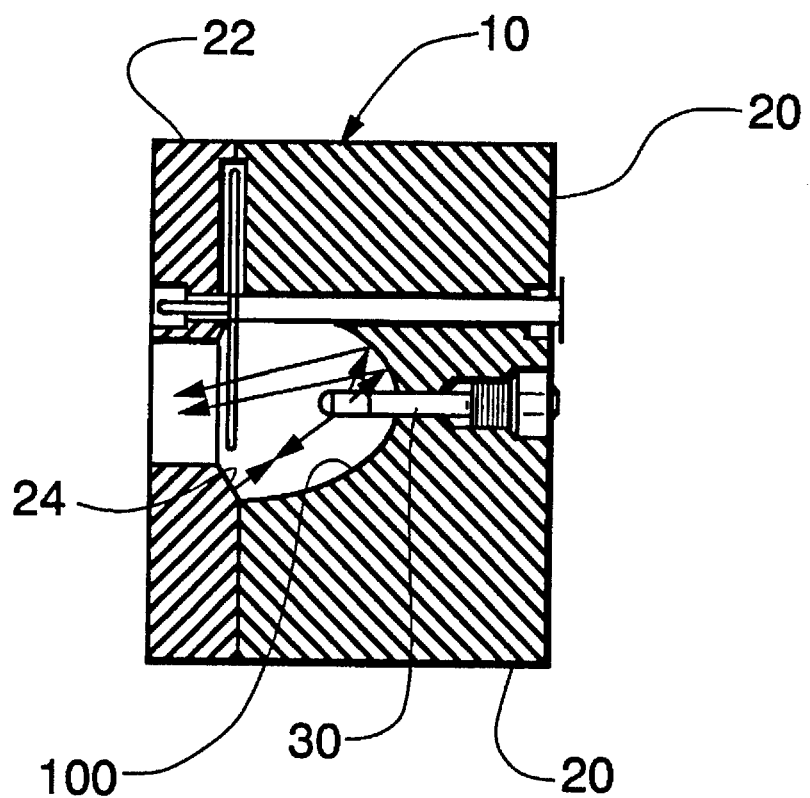
FIG. 7 is a diagrammatic view of a collector having parabolic and spherical reflection surfaces.

Another option for the geometry of the first block 20 section is an ellipsoidal surface 100 seen in FIG. 7. In this case, the ellipsoid would have one focus located at D1 and the other at D2. The advantage to utilizing an ellipsoid over a sphere is the reduction of aberrations such as spherical aberration encountered when utilizing a sphere in this manner. However, so long as the blur diameter resulting from the sample compartment, remains smaller in scale than the entrance of the light guide, aberrations may be neglected. The chief disadvantage to utilizing an aspherical (ellipsoid or variation of an ellipsoid with additional deformations to allow for aberration correction) is the associated higher manufacturing costs.

The second portion of the collecting optics should always take the form of a sphere. This spherical mirror will be positioned with its center of curvature coaxial with the center of the emitter. The result of such an arrangement is that all energy which exceeds the acceptance of the first shell half, will reflect from the second shell half and return towards a section of the first shell portion which allows for the energy to be focused into the specimen holder, as seen in FIG. 3.

In the embodiment shown in FIG. 1, the emitter may be an infrared (IR) energy source which can be the equivalent of a heated wire operating at 660°–800° C. This gives a broad band of IR radiation from 2–15 microns which is collected into a narrow beam of IR energy by the reflective surfaces. As seen in FIG. 3, the collection of light from a finite source by the mirror segment up to NA (numerical aperture) of 1.0+ is focused into the entrance aperture of the specimen holder. The collection efficiency is increased beyond 1.0+ NA by the addition of the second concave collecting optic which redirects the energy from angles exceeding the 1.0+ NA condition, towards the focus of the first mirror segment. Thus, the first segment can re-collect this energy and direct it to the entrance aperture of the specimen holder. Therefore, the collector optics ensure a high collection ratio of energy from the emitter.

The specimen will encode the incident optical energy with information regarding its molecular physical properties. As is known, optical energy of particular specular characteristics will be affected by the specimen composition, therefore, the optical energy emergent from the specimen holder will carry with it information which indicates the molecular nature of the specimen.

The windows for the specimen holder desirably utilize materials which allow the transmission of optical energy which falls within the optical wavelength bandwidth of interest. For instance, windows would be comprised of barium fluoride for an infrared detection apparatus. This material is selected due to its ability to transmit IR energy with no absorption in the regions of interest to the analysis.

As previously indicated, the non-imaging optical member is of a geometry which reduces the angle of incident rays as they traverse its length. The concept of these optics can be envisioned as a collection of points which define a tangent to the angle of the light accepted as a lesser angle.

As a result of the angular orientation of the optics, the degree of perpendicularity between the rays exiting the non-imaging optical member and the normal to the optical filter and photodetector is increased. Narrow wavelength band optical filters are designed to allow for transmission of a relatively small selective region of wavelengths. This may be accomplished through the stacking of different layers of transmissive materials. Energy which strikes the surface of the filter at angles departing from the normal to the surface will have a path length in the medium defined by the skew path through a particular filter layer. The greater is this angle, the larger is the error. The filter allows for the transmission of wavelengths which produce a certain pathlength in the medium. The energy of a lesser wavelength which is at a higher angle of incidence on the filter will look to the filter as wavelengths with the proper pathlength. This phenomenon known as "blue shifting" explains how these wavelengths of a lower angle (bluer) are allowed to pass therethrough. Thus, the non-imaging optical member reduces this inherent error. Some typical formulas for "non-imaging" optics can be found in the text: "The Optics of Non-Imaging concentrators" by Welford & Winston, published by Academic Press.

Figure 8:
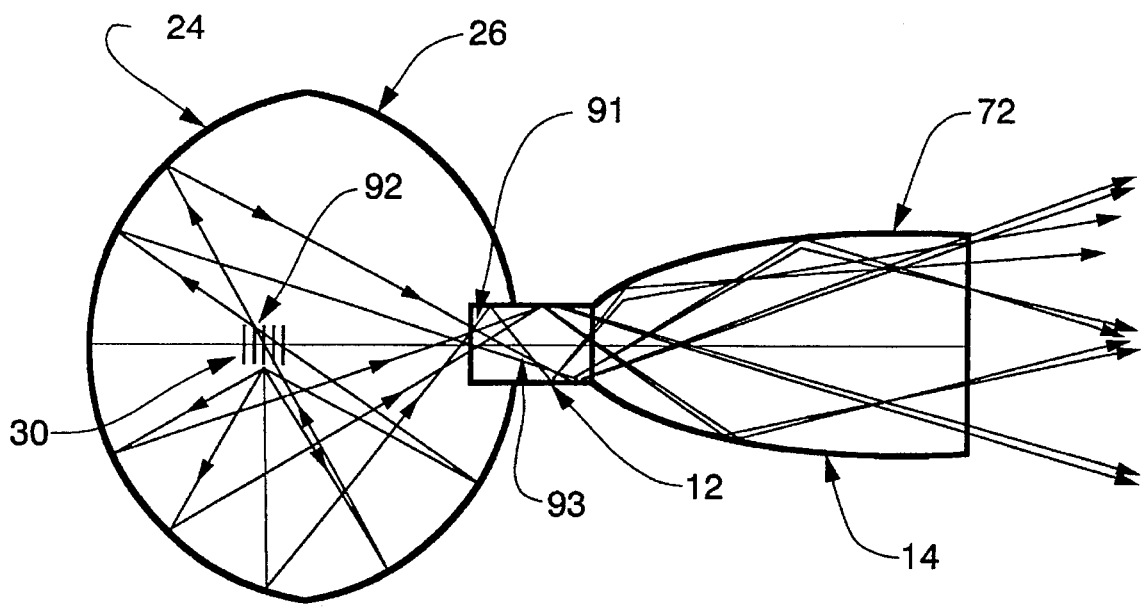
FIG. 8 is a diagrammatic view of a source, concave mirrors, homogenizing element, and non-imaging optic, showing traces of the light rays passing therethrough.

Regarding FIG. 8, therein schematically illustrated are ray traces showing light rays emitted by the source 30, being reflected by the first concave mirror 24 and the second concave mirror 26 to the "optional" light guide 12 which functions as an homogenizing element to make the intensity of the emerging light more uniform. The light rays pass into the non-imaging optical member 14 which is positioned to collect substantially all of the light. The light rays are reflected from the surface defining the passage through the member 14 so that they exit at a relatively shallow angle relative to the optical axis 72 of the system shown in FIGS. 4a and 4b.

As shown in FIG. 8, light from source 30 reflects from the first concave mirror 24 to produce the first image 91 at the entrance to the "optional" light guide 12. The second concave mirror 26 collects light from source 30 which exceeds the boundary of the first mirror 24 and produces a second image 92 proximate to light source 30. The first concave mirror 24 also re-images the light collected from second mirror 26 to produce a third image 93 within the light guide 12 proximate to the first image 91. The non-imaging reflector 14, which may be a compound parabolic concentrator, receives both images 91 and 93 through an aperture 94 and concentrates the light of these images along its length. This system collects a solid angle up to $4\pi$ stiradians of light from source 30.

The illumination system of this invention may be used in the following applications:

slide projectors, projection television units, microscope illuminators, all types of "examination" lamps, filter IR, VIS, UV, NIR spectrometers, Raman spectrometers, fluorescence spectrometers, refractometers, interferometers, general vehicle lights, HUD lights for aircraft, Dolan-Jenner fiberoptic illuminators, otoscopes, Schlieren System devices, search lights, and as general class laser cavities.

Specifically, the illumination system of the invention is easily adapted to provide:

1. An enhanced infrared signal delivery system for FTIR (Fourier TRansform IR) spectroscopy systems. For FTIR spectrometer benches, the system provides a substantially increased amount of available signal for analysis, and, thus allows for a lower temperature source for operation. As a remote energy source for FTIR microscopes, and in testing systems which require remote IR illumination sources, the compact, high-efficiency design of the illumination system provides obvious benefits.

2. A general visual illumination source for use in visual microscopy where it acts as an all-reflective, low-cost system for collection of light from a white light source (e.g. Halogen light source) and for directing the light onto a microscope sample; in fiberoptic endoscope/borescope systems where the invented system delivers substantially more energy into the fiber for illumination, and a source of bright white light illumination for security systems, flashlights and floodlight style systems.

The illumination system of this invention is also useful in any application where a limited amount of Electro magnetic energy is available for illumination, e.g. UV Fluorescence.

Furthermore, the system could be used entirely in reverse to produce a system with enhanced capability to deliver energy to a sample from almost 360 degrees.

This system has the ability to produce illumination beams of low angular divergence. A direct function of the non-imaging optic is to transform, by some factor, the angle at which light enters the input aperture to some lesser angle upon departure through the exit aperture. Generally, the greater the angle of divergence entering a non-imaging optic, the greater the angle exiting the non-imaging optic.

The illuminating systems of the prior art produce angles as great as 90 degrees to the non-imaging optics centerline, entering the aperture. In contrast, the geometry of the invented system allows for the rays of greatest divergence entering the nonimaging optic of approximately 65 degrees; and, thus, is much more efficient in the concentration of energy than the designs of the prior art.

Since divergence angle, alignment sensitivity, size, and fabrication cost are the chief concerns in the production of efficient illumination systems, the system of this invention provides for the total $4\pi$ steradian (solid angle) collection of light emanating from an optical light source and directs this energy in a manner which reduces the divergent angles to such an extent that operation of common optical systems is markedly improved.

I claim:

1. An illumination system comprising:

a light source which emits light;

a first concave reflective surface or mirror having a center of curvature positioned to collect light from said source at a point remote from said source; a second concave reflective surface or mirror having a center of curvature which collects light from said source within the second half space of emitted light, said second mirror reflects or images said second half space of light to produce a second image of said light source at a point proximate to said light source where said first concave mirror reflects or reimages the light collected from said second concave mirror to provide a third image of said light source at the remote point where said first image is produced; and, a non-imaging reflector having an input aperture positioned to receive substantially all of the light from said first and third images of said light source.

2. The illumination system as in claim 1 wherein said second reflecting concave mirror is a spherical reflecting surface.

3. The illumination system as in claim 1 wherein a light energy homogenizing element having entrance and exit apertures is placed within its entrance aperture positioned to collect substantially all the light from said first and second concave mirrors, and its exit aperture positioned to direct the collected light to said non-imaging reflector.

4. The illumination system as in claim 1 wherein said light source emits light in the infrared wavelength.

5. The illumination system as in claim 1 wherein said light source, said centers of curvature of said mirrors and all of said images lie substantially in a common line.

6. The illumination system as in claim 1, wherein said non-imaging reflector has a configuration selected from a group consisting of conical, generally aspherical and spline.

* * * * *